United States Patent
De Lange

(10) Patent No.: US 8,865,900 B2
(45) Date of Patent: *Oct. 21, 2014

(54) METHYLTETRAZOLE SULFIDES AND SULFONES

(75) Inventor: Ben De Lange, Echt (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/979,755

(22) PCT Filed: Jan. 13, 2012

(86) PCT No.: PCT/EP2012/050471
§ 371 (c)(1),
(2), (4) Date: Jul. 15, 2013

(87) PCT Pub. No.: WO2012/098050
PCT Pub. Date: Jul. 26, 2012

(65) Prior Publication Data
US 2013/0296563 A1    Nov. 7, 2013

(30) Foreign Application Priority Data

Jan. 18, 2011 (EP) .................................. 11151280
Oct. 11, 2011 (EP) .................................. 11184697

(51) Int. Cl.
C07D 239/02 (2006.01)
C07D 257/00 (2006.01)
C07D 405/06 (2006.01)
C07D 405/12 (2006.01)
C07D 413/12 (2006.01)
C07D 405/14 (2006.01)
C07D 419/12 (2006.01)

(52) U.S. Cl.
CPC ............ *C07D 405/12* (2013.01); *C07D 405/06* (2013.01); *C07D 413/12* (2013.01); *C07D 405/14* (2013.01); *C07D 419/12* (2013.01)
USPC ......................................... 544/332; 548/251

(58) Field of Classification Search
None
See application file for complete search history.

(56) References Cited

U.S. PATENT DOCUMENTS

2012/0136151 A1*   5/2012   Lee et al. ..................... 544/297

FOREIGN PATENT DOCUMENTS

WO    WO 01/96311    12/2001
WO    WO 02/098854    12/2002

OTHER PUBLICATIONS

American Chemical Society (ACS). STN Chemical Abstract Service (CAS) RN Database #: 1257341-70-0, first available to the public on Dec. 22, 2010.*
International Search Report for PCT/EP2012/050471 mailed Mar. 27, 2012.
J. Muñoz-Muriedas et al., "Hydrophobic Molecular Similarity from MST Fractional Contributions to the Octanol/water Partition Coefficient", Journal of Computer-Aided Molecular Design, vol. 19, No. 6, Jun. 1, 2005, pp. 401-419.
N.V. Harris et al., "Acyl-COA: Cholesterol O-Acyl Transferase (ACAT) Inhibitors. 1.2-(Alkylthio)-4,5-Diphenyl-1H-Imidazoles as Potent Inhibitors of CAT", Journal of Medicinal Chemistry, American Chemical Society, vol. 35, Jan. 1, 1992, pp. 4384-4392.
D.R. Sliskovic et al., "Inhibitors of Cholesterol Biosynthesis. 4. trans-6-[2-( Substituted-quinolinyl) ethenyl] tetrahydro-4-hydroxy-2H-pyran-2-ones, a Novel Series of HMG-CoA Reductase Inhibitors[1]", Journal of Medicinal Chemistry, vol. 34, No. 1, 1991, pp. 367-373.

* cited by examiner

*Primary Examiner* — Noble Jarrell
*Assistant Examiner* — John S Kenyon
(74) *Attorney, Agent, or Firm* — Nixon & Vanderhye P.C.

(57) ABSTRACT

The present invention relates to a process for the preparation of a 1-methyl-1H-tetrazole-5-thio derivative comprising reaction of a halomethyl substrate with 1-methyl-H-tetrazole-5-thiol to obtain a thio-ether compound, and oxidizing the thio-ether compound to the corresponding sulfone. In case of a chiral halomethyl substrate, the resulting chiral diol sulfone derivative is suitable as a building block for statin type compounds.

9 Claims, No Drawings

METHYLTETRAZOLE SULFIDES AND SULFONES

This application is the U.S. national phase of International Application No. PCT/EP2012/050471 filed 13 Jan. 2012 which designated the U.S. and claims priority to EP 11151280.2 filed 18 Jan. 2011, and EP 11184697.8 filed 11 Oct. 2011, the entire contents of each of which are hereby incorporated by reference.

FIELD OF THE INVENTION

The present invention relates to a process for the preparation of a 1-methyl-1H-tetrazole-5-thio derivative comprising reaction of a halomethyl substrate with 1-methyl-1H-tetrazole-5-thiol to obtain a thio-ether compound, and oxidizing the thio-ether compound to the corresponding sulfone. In case of a chiral halomethyl substrate, the resulting chiral diol sulfone derivative is suitable as a building block for statin type compounds.

BACKGROUND OF THE INVENTION

Chiral diol sulfones are advanced intermediates used in the preparation of statins, a class of compounds useful as HMG CoA reductase inhibitors. In particular, chiral diol sulfones are employed in preparing statins in which an unsaturated carbon-carbon bond is to be formed such as is the case in the antilipemic drugs cerivastatin, fluvastatin, pitavastatin and rosuvastatin.

A method for preparing chiral diol sulfones is described in WO 2002/098854 and WO 2001/096311. In these citations, a sulfone is prepared from an alcohol, more in particular tert-butyl 2-((4R,6S)-6-(hydroxymethyl)-2,2-dimethyl-1,3-dioxan-4-yl)acetate known as "Kaneka alcohol". The preparation of such an alcohol is described in EP 1024139.

The synthesis of the sulfone in the prior art has a disadvantage, in that trifluoromethanesulfonic anhydride or another sulfonic acid derived activating agent is used to activate the alcohol function to an extent that a nucleophilic attack with a thiol is possible. Trifluoromethanesulfonic anhydride is an extremely hazardous and expensive component, which causes costly work-up procedures due to environmentally problematic waste streams. In WO 2010/140765 this problem has been addressed by direct reaction of a halomethyl derivative of a very specific and highly sterically hindered 2-methyl-1-phenylpropan-2-yl ester. Although this represents a first example of a direct nucleophilic attack by a thiol compound on a halide, the bulkiness of the ester group inherently also prevents the side reaction of unwanted substitution of the ester moiety leading to unwanted thio-ester.

The prior art also advocates the use of sterically hindered chiral diol sulfones such as those based on phenyl- or tert-butyl substituted tetrazoles. The rationale behind this is that only these bulky compounds are suitable to control the E/Z-ratio in subsequent reactions such as the Julia-Kocienski olefination.

It is an object of the present invention to provide a process, in which not only the use of an activating agent like trifluoromethanesulfonic anhydride is omitted but which is also applicable to esters of sterically unhindered and/or small alcohols such as butyl esters, ethyl esters, methyl esters and propyl esters.

DETAILED DESCRIPTION OF THE INVENTION

In a first aspect of the invention, a compound of formula (1) or the corresponding lactone form (1') can be used as starting material

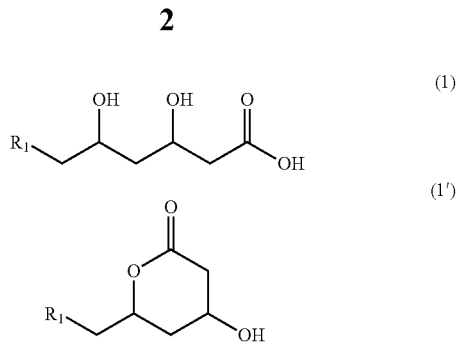

wherein $R_1$ stands for halogen, like bromine or chlorine, preferably chlorine.

Prior to use in the process of the invention the hydroxyl groups and the carboxyl group of the above compounds may be protected as ketal and ester as outlined in general formula (1a) or as lactone and ether as outlined in general formula (1b)

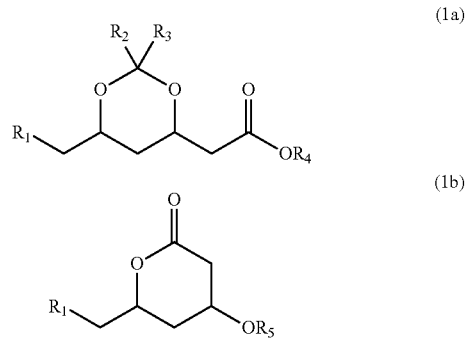

wherein $R_2$ and $R_3$ each independently stand for an alkyl with for instance 1 to 12 C-atoms, preferably 1 to 6 C-atoms, an alkenyl with for instance 1 to 12 C-atoms, preferably 1 to 6 C-atoms, a cycloalkyl with for instance 3 to 7 C-atoms, a cycloalkenyl with for instance 3 to 7 C-atoms, an aryl with for instance 6 to 10 C-atoms or an aralkyl with for instance 7 to 12 C-atoms, each of $R_2$ and $R_3$ may be substituted and wherein $R_2$ and $R_3$ may form a ring together with the C-atom to which they are bound, use being made of a suitable acetal forming agent, in the presence of an acid catalyst, for example as described in WO 2002/06266. The groups $R_2$ and $R_3$ are for example halogens or hydrocarbon groups with for instance 1 to 10 C-atoms, optionally containing one or more heteroatoms, for instance Si, N, P, O, S, F, Cl, Br or I. In practice, $R_2=R_3$ is methyl is most preferred. In the compound of general formula (1a) $R_4$ is an alkyl or alkenyl group with one, two, three or four carbon atoms. Such relatively small substituents are favorable since they have a high so-called 'carbon economy', i.e. the use of organic material is lower than is the case with more complex protecting groups. Suitable examples are allyl, iso-butenyl, n-butyl, sec-butyl, tert-butyl, ethyl, methyl, n-propyl, iso-propyl and vinyl. Preferably $R_4$ is a group that is easily introduced, small and easily removed under acidic conditions such as ethyl, methyl or iso-propyl. In the compound of general formula (1b) $R_5$ is hydrogen or an alcohol protecting group. Such a group can be any alcohol protecting group known to the skilled person such as described in, for example "Protective Groups in Organic Synthesis" (T. W. Greene, 1981, Wiley-Interscience Publication, ISBN 0-471-05764-9). These protecting groups are for example esters or ethers. These protecting groups are preferred because in the final stage of conversion of these building blocks to statins, these generally acid labile or basic labile (in the case of esters) protecting groups have the advantage to be removed either simultaneously with the opening of the lactone ring or by a pH shift. Hence, suitable groups $R_5$ are allyl, benzyloxymethyl, tert-butoxymethyl, tert-butyl, methoxymethyl, 1-ethoxyethyl, methoxyethoxymethyl, 4-methoxytetrahydropyranyl, methylthiomethyl, 1-(iso-propoxy) ethyl, tetrahydrofuranyl, tetrahydropyranyl, 2-methoxypropanyl, 1-propenyl, acetate, chloroacetate or benzoate.

The compounds of formula (1) and (1'), and hence the compounds of formula (1a) and (1b) can be either enantiomerically pure or enriched in one of the enantiomers or racemic.

The compounds of formula (1a) or (1b) are reacted with 1-methyl-1H-tetrazole-5-thiol (MTT) or a derivative thereof to give a compound of general formula (2a) or (2b), respectively with $R_2$, $R_3$, $R_4$ and $R_5$ as defined above.

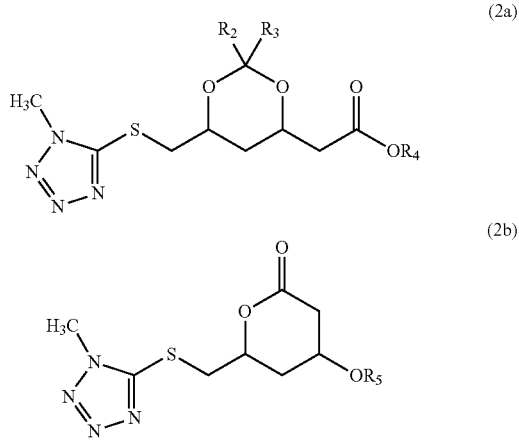

Suitable derivatives of MTT salts like sodium, potassium or lithium, or an ammonium salt like tetraalkylammonium, or a phosphonium salt like tetraalkylphosphonium. The MTT moiety was found to be suitable for a one-pot or modified Julia-Kocienski olefination. This is quite unexpected in view of the fact that the prior art, for example WO 2001/096311, WO 2002/098854 and a review by Aïssa (Eur. J. Org. Chem. 2009, 1831-1844), advocate the use of more hindered thiols. Advantageously, and in contrast to prior art bulky thiols, MTT is easily accessible (no need for separate synthesis) and quite inexpensive. The Julia-Kocienski olefination is a reaction in which a sulfone is reacted with an aldehyde to form an olefinic (double) bond. The original Julia olefination requires two steps. In the modified reaction (Julia-Kocienski olefination), the intermediate obtained in the reaction with an aldehyde undergoes spontaneous elimination to give the olefin.

The reaction from (1a) or (1b) to (2a) and (2b) respectively, will take place under suitable conditions wherein it is generally important to preclude harsh conditions (like temperatures above 130° C. or exceedingly long reaction times or application of strongly basic or acidic conditions) in order to preclude degradation of the starting compound or the thiol obtained. Suitable reaction conditions are temperatures about 50° C. or higher, preferably about 80° C. or higher, and more in particular about 100° C. or higher. Generally, the temperature will be about 150° C. or lower, preferably about 140° C. or lower, and more in particular about 130° C. or lower. In case a temperature at the higher end-range is chosen, care should be taken to choose the time period such, that limited degradation occurs. Limited degradation is less than 10% of the starting halomethyl compound of general formula (1a) or (1b), preferably less than 5%, more in particular less than about 3%. Generally, a reaction time of less than about 20 h, preferably less than about 10 h should be possible in case the reaction conditions are chosen properly. However, the time period is not critical, and may be up to 30 h or longer. Generally, the reaction takes longer than about 1 h, but this is strongly dependant on the reaction conditions, reaction engineering aspects (like reactor design or application of rate-accelerating means like application of ultrasound or microwave irradiation) and amounts of reagents used, and this is not critical.

The reaction to obtain the thio-ether can be performed in a solvent. Suitable solvents are dimethylsulfoxide (DMSO), N-methylpyrrolidone (NMP), dimethylformamide (DMF), sulfolane, acetonitrile, glymes (alkyl-capped or uncapped mono-, oligo-, or poly-ethylene glycol ethers of varying chain length) or other polar non-protic solvents or alcohols like methanol, ethanol, 2-propanol, or halogenated hydrocarbons like dichloromethane, chloroform, 1,2-dichloroethane, optionally in combination with non-polar solvents like toluene or methyl tert-butyl ether (MTBE).

The concentration of halomethyl starting compound of general formula (1a) or (1b) is generally about 10 wt % or higher, preferably about 30 wt % or higher, more in particular about 40 wt % or higher. Preferably, the reaction is carried out with a relatively high concentration of halomethyl starting compound of general formula (1a) or (1b) of 70 to 99 wt %.

It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). These phase transfer-catalysts are also very suitable for use in mono-phasic solvent systems. Another class of suitable solvents comprises ionic liquids like, for example, 1,3-dialkyl imidazolium salts or N-alkyl pyridinium salts of acids like hexafluorophosphoric acid or tetrafluoroboric acid or trifluoromethane sulfonic acid, or with $(CF_3SO_2)_2N^-$ as anionic counterpart.

The amounts of reagents can be chosen from a wide range. It is preferred to use a rate-enhancing excess of MTT, as the excess MTT that remains after reaction with the halomethyl derivative can be easily removed by washing with water at high pH. The molar amount of MTT to halogen compound generally is about 0.5 to 1 or higher, preferably 1 to 1 or higher, more preferably 1.1 to 1 or higher. Generally, the amount of MTT to halogen compound will be 3 to 1 or lower, preferably 2 to 1 or lower, most preferably 1.5 to 1 or lower. Preferably excess MTT is recovered for re-use.

The thio-ether compound of general formula (2a) or (2b) can be isolated from the reaction mixture, or the mixture can be used as such in a subsequent oxidation reaction. Preferably, the reaction mixture is treated so as to remove excess MTT or excess halogen compound as the case may be. Any excess MTT can be easily removed by extraction with water at pH higher than 7, preferably higher than 8, more preferably of about 9 or higher. Suitable extraction agents are for example saturated caustic soda solution, saturated bicarbonate solution, or diluted sodium hydroxide solution. After extraction, the thio-ether compound of general formula (2a) or (2b) can be isolated by removal of the solvent by distillation, or by crystallization or precipitation, e.g. by addition of (or solvent switch to) an anti-solvent like hexane, heptane, iso-octane, or water. It is however not necessary to remove the solvent, as the oxidation can be performed in the same solvent. It is however preferred, to remove water from the reaction mixture, in case water interferes with the oxidation reaction. Hence, in a preferred embodiment of the invention, the oxidation is carried out without purification of the thio-ether compound of general formula (2a) or (2b), more preferably in the same solvent as was used in the etherification reaction.

According to the process of the invention, a halogen derivative can be used as starting compound. This is advantageous because the Kaneka alcohol generally is prepared from such a halogen derivative. Therefore, the present invention provides a process, in which additional steps in the prior art are made obsolete if the chiral diol sulfone is to be used in a Julia-Kocienski olefination.

It was unexpected, that the thio-ether compound of general formula (2a) or (2b) could be prepared in this way, because a nucleophilic attack on a halomethyl group (in particular a chloromethyl group) in the presence of an alkoxy substituent in beta-position to the halogen is known to be extremely difficult [cf. a) Methoden der Organischen Chemie (Houben-Weyl), vol. V/4, 1960, p. 700; b) M. E. Jung et al, J. Org. Chem. 1998, 63, 347-355 and ref. 17 cited therein; c) D. G. Bourke et al., Aust. J. Chem. 1996, 49, 425-434]. This holds especially in cases where said alkoxy substituent is part of a cyclic ether moiety like the 1,3-dioxane moiety as exemplified in the compound of formula (1a). Drastic reaction conditions like a 20-fold excess of the nucleophile and/or reaction times of up to weeks are necessary to obtain a useful conversion [cf. a) WO 2003/004459 and references cited therein, b) W. E. Willy et al., Bull. Chem. Soc. Japan 1976, 49, 1989-1995 (see table 1, entry 11); c) S. D. Rychnovsky et al, J. Org. Chem. 1992, 57, 1559-1563; d) M. Kabeya et al., Tetrahedron 1997, 53, 9777-9788]. On the other hand, harsh conditions will lead to decomposition and/or to racemization (or epimerization, respectively) of the diol function in the case of compounds like shown in formula (1). Therefore, it was unexpected, that this reaction could be carried out under mild conditions that allowed more than 80% yield, and even more than 90% yield in combination with less that 5% degradation of the starting compound, or even less than 3% degradation.

Where nucleophilic attack on a halomethyl group appears successful in WO 2010/140765, this could not be anticipated in the presence instance where the substrate molecules of general formula (1a) and (1b) all have small and relatively unhindered carboxylic acid protecting groups such as methyl or iso-propyl. It is well-known that such small and unhindered moieties easily undergo degradation. Moreover, especially in the presence of thiols such small moieties can form thioesters. These unwanted side reactions are not to be predicted for highly sterically hindered esters such as the 2-methyl-1-phenylpropan-2-yl ester presented in WO 2010/140765.

The thio-ether compound of general formula (2a) or (2b) is oxidized in manners known in the art, for example by oxidation with hydrogen peroxide or other oxidants like peracids (e.g. 3-chloroperoxybenzoic acid, peroxyacetic acid, monoperoxyphthalic acid), bleach, tert-BuOCl, perborates, N-oxides, permanganate, chromate, chlorate, bromate, perchlorate, periodate, tert-butyl hydroperoxide, oxone, peroxodisulfates and air/oxygen. If necessary, the oxidation can be carried out in the presence of an appropriate catalyst, such as salts or oxides of the metals V, Ce, Mn, Ni, Fe, Cu, Os, Mo, W, Re, or Ru or organic catalysts like iso-butyraldehyde in the case of air/oxygen or tetramethylpiperidine N-oxide (TEMPO) in the case of bleach. The resulting sulfones are of general formula (3a) and (3b), respectively, with $R_2$, $R_3$, $R_4$, $R_5$ and $R_6$ as defined above.

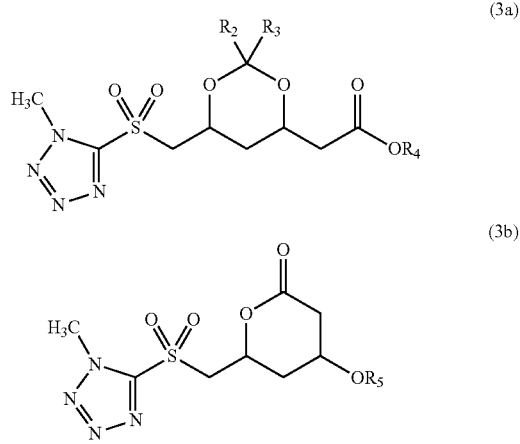

The oxidation generally is performed in a solvent, such as dichloromethane, chloroform, 1,2-dichloroethane, methanol, ethanol, 2-propanol, acetonitrile, acetic acid, toluene, water, NMP, DMSO, DMF, tetrahydrofuran (THF), or MTBE. It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). Another class of suitable solvents comprises ionic liquids like, for example, 1,3-dialkyl imidazolium salts or N-alkyl pyridinium salts of acids like hexafluorophosphoric acid or tetrafluoroboric acid or trifluoromethane sulfonic acid, or with $(CF_3SO_2)_2N^-$ as anionic counterpart. Generally, a reaction temperature of about −20° C. or higher is effective.

Preferably, a temperature of about 0° C. or higher is applied, more preferably a temperature close to ambient temperature (18-25° C. i.e. around 20° C.). A temperature of about 150° C. or lower generally is effective to bring about the oxidation. Generally, the reaction temperature will be about 100° C. or lower, more preferably about 60° C. or lower, most preferably about 40° C. or lower. The molar amount of oxidant to thio-ether generally is about 1 to 1 or higher, preferably about 2 to 1 or higher, more preferably about 3 to 1 or higher. Generally, the amount of terminal oxidant to thio-ether will be about 20 to 1 or lower, preferably about 10 to 1 or lower, most preferably about 5 to 1 or lower.

The sulfone of general formula (3a) or (3b) can be isolated by aqueous extraction of excess oxidant/catalyst and subsequent removal of the solvent by evaporation. If water-miscible solvents like alcohols or aprotic polar solvents are applied as reaction medium, the reaction mixture can be partitioned between an aqueous and an organic phase prior to this operation, in order to extract the solvent to the aqueous phase. If ionic liquids are applied as reaction medium, the sulfone can be isolated by extraction with an organic solvent immiscible with the ionic liquid, followed by evaporation of the solvent. Alternatively, the sulfone can be isolated from the reaction mixture by precipitation or crystallization, e.g. by addition of (or solvent switch to) an anti-solvent like hexane, heptane, iso-octane, or water. If desired, purification of the sulfone can be performed by chromatography or, preferably, by re-crystallization from (or trituration with) a suitable solvent, like 2-propanol or another solvent, depending on the residues $R_2$, $R_3$, $R_4$ and $R_5$ used with the initial halomethyl compounds of formula (1a) or (1b).

In one embodiment, the sulfone of general formula (3a) or (3b) is treated with an aldehyde $R_6$—CH=O, in which $R_6$ is chosen so as to obtain suitable precursors to useful statin-type compounds including pitavastatin, rosuvastatin, fluvastatin, and cerivastatin, or in which $R_6$ is a suitable precursor to these moieties (cf. WO 2002/098854 and WO 2001/096311). Preferred examples of aldehyde $R_6$—CH=O are 4-(4-fluorophenyl)-2,6-diisopropyl-5-(methoxymethyl)nicotinaldehyde, 3-(4-fluorophenyl)-1-isopropyl-1H-indole-2-carbaldehyde, 2-cyclopropyl-4-(4-fluorophenyl)quinoline-3-carbaldehyde and N-(4-(4-fluorophenyl)-5-formyl-6-isopropylpyrimidin-2-yl)-N-methylmethanesulfonamide as these aldehydes are the precursors for cerivastatin, fluvastatin, pitavastatin and rosuvastatin, respectively.

The so-called Julia-Kocienski olefination between compounds (3a) or (3b) and aldehyde $R_6$—CH=O preferably is carried out in the presence of a base, preferred examples of which are lithium hydride, potassium hydride, sodium hydride, lithium hexamethyldisilazane (LiHMDS), sodium hexamethyldisilazane (NaHMDS), potassium hexamethyldisilazane (KHMDS), solid potassium hydroxide, solid sodium hydroxide, metal alkoxides, such as sodium methoxide, lithium methoxide and potassium methoxide, lithium tert-butoxide, potassium tert-butoxide, sodium tert-butoxide, lithium bis-trimethylsilylamide (LiN(TMS)$_2$), sodium bis-trimethylsilylamide (NaN(TMS)$_2$), potassium bis-trimethylsilylamide (KN(TMS)$_2$), sodium amide, P4-tBu and 1,8-diazabicyclo[5.4.0]undec-7-ene (DBU) and the like. Whereas the E/Z-ratio in the final product depends on various parameters, such as type of base, thio-substituent ($R_6$) and solvents, as for instance outlined in P. R. Blakemore, W. J. Cole, P. J. Kocienski and A. Morley, Synlett 1998, 26-28, this ratio normally varies between 40:60 and 80:20 in customary solvents such as diethyl ether, dimethoxyethane, tetrahydrofuran and toluene.

Surprisingly it was found that in the condensation reaction of the present invention, i.e. starting from compounds of general formula (3a) and (3b) and aldehydes $R_6$—CH=O there was a marked difference between lithium-comprising bases and sodium-comprising bases where the latter strongly favored extremely high E/Z-ratio's. For example, when using LiHMDS an E/Z-ratio of 70:30 was achieved whereas the use of NaHDMS led to an E/Z-ratio of >99:1. This is advantageous as the E-configuration is the required configuration in cerivastatin, fluvastatin, pitavastatin and rosuvastatin. Hence, the use of a sodium-comprising base precludes laborious removal and/or recycling of undesired Z-isomer.

(4a)

(4b)

(5)

Following the Julia-Kocienski olefination between compounds (3a) or (3b) and aldehyde $R_6$—CH=O the resulting products (4a) and (4b), respectively may be isolated and purified after which they are deprotected to give product (5). Alternatively deprotection may be carried out without isolation and/or purification of intermediate products (4a) and (4b). Deprotection is carried out according to procedures known to the skilled person, for instance by using acid such as hydrochloric acid as described in U.S. Pat. No. 6,844,437 or WO 2007/000121.

In a second aspect, the invention relates to a novel compound of general formula (6)

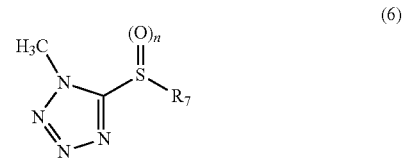

(6)

wherein n is 0, 1 or 2 and wherein $R_7$ is a radical of formula (7) or (8)

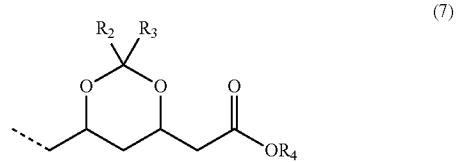

(7)

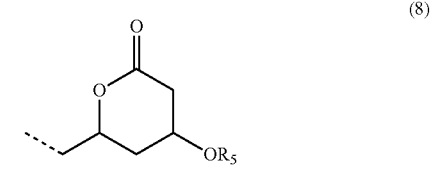

(8)

wherein $R_2$, $R_3$, $R_4$ and $R_5$ are as described above.

The compounds of the second aspect of the invention are well suited as easily accessible intermediates in the synthesis of statins such as cerivastatin, fluvastatin, pitavastatin and rosuvastatin and may be prepared according to the process of the first aspect of the invention.

EXAMPLES

Example 1

Preparation of (4R,6S)-6-(chloromethyl)-2,2-dimethyl-1,3-dioxan-4-yl)acetic acid methyl ester (B) from (4R,6S)-6-(chloromethyl)-4-hydroxytetrahydropyran-2-one (A)

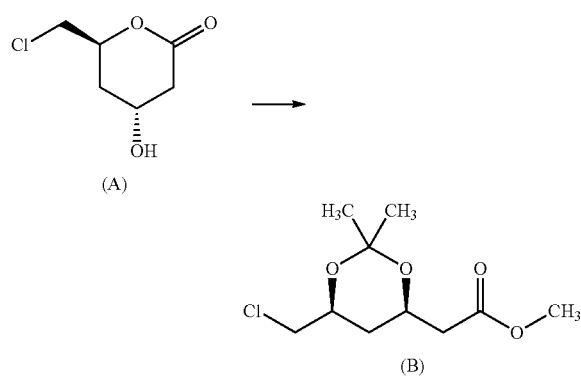

(4R,6S)-6-(chloromethyl)-4-hydroxytetrahydropyran-2-one (Compound A, 88 g, 0.53 mol) was added in 45 min to a solution of 1.0 g p-toluenesulfonic acid in 250 mL of dimethoxypropane. After stirring for 2 h at 20-22° C., 200 mL of ethyl acetate and 100 mL of saturated aqueous $NaHCO_3$ were added. The phases were separated and the organic phase was washed with 10% aqueous $NaHCO_3$ (2×100 mL). After drying over $Na_2SO_4$, the organic phase was concentrated to give (4R,6S)-6-(chloromethyl)-2,2-dimethyl-1,3-dioxan-4-yl)acetic acid methyl ester as a brownish oil (Compound B, 127.2 g, ~quantitative yield)

Example 2

Preparation of 2-((4R,6S)-2,2-dimethyl-6-((1-methyl-1H-tetrazol-5-ylthio)methyl)-1,3-dioxan-4-yl)acetic acid methyl ester (C) from (4R,6S)-6-(chloromethyl)-2,2-dimethyl-1,3-dioxan-4-yl)acetic acid methyl ester (B) and 1-methyl-1H-tetrazole-5-thiol (MTT)

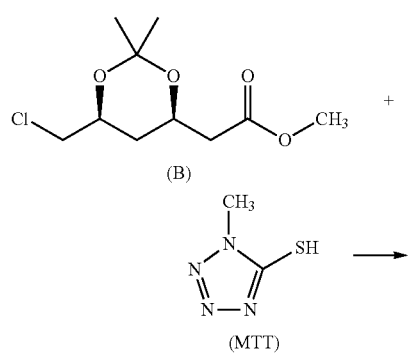

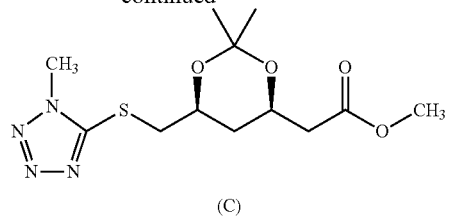

(4R,6S)-6-(Chloromethyl)-2,2-dimethyl-1,3-dioxan-4-yl)acetic acid methyl ester (Compound B, 47.2 g, 0.20 mol) was dissolved in 150 mL of N-methylpyrrolidone. Then $NaHCO_3$ (23.5 g, 0.28 mol) and tetra-n-butyl ammonium bromide (0.5 g) were added. To the stirred mixture was added 1-methyl-1H-tetrazole-5-thiol (MTT, 27.8 g, 0.24 mol). The mixture was heated to 90° C. and kept at this temperature for 18 h. After cooling to 20-25° C., methyl-tert-butyl ether was added (500 mL) and saturated aqueous $NaHCO_3$ (250 mL). Some precipitation was removed by filtration and washed with 100 mL of methyl-tert-butyl ether. The filtrate was washed with 200 mL of saturated aqueous $NaHCO_3$. After drying over $Na_2SO_4$, the organic phase was concentrated to give 2-((4R,6S)-2,2-dimethyl-6-((1-methyl-1H-tetrazol-5-ylthio)methyl)-1,3-dioxan-4-yl)acetic acid methyl ester as a solid (Compound C, 45.2 g, yield 71%). $^1$H NMR (300 MHz, $CDCl_3$) δ 4.40-4.22 (m, 2H), 3.92 (s, 3H), 3.68 (s, 3H), 3.40 (dd, 2H), 2.48 (dd, 2H), 1.74 (dt, 1H), 1.42 (s, 3H), 1.39-1.29 (m, 1H), 1.35 (s, 3H).

Example 3

Preparation of 2-((4R,6S)-6-((1-methyl-1H-tetrazol-5-ylsulfonyl)methyl)-2,2-dimethyl-1,3-dioxan-4-yl)acetate methyl ester (D) from 2-((4R,6S)-2,2-dimethyl-6-((1-methyl-1H-tetrazol-5-ylthio)methyl)-1,3-dioxan-4-yl)acetic acid methyl ester (C)

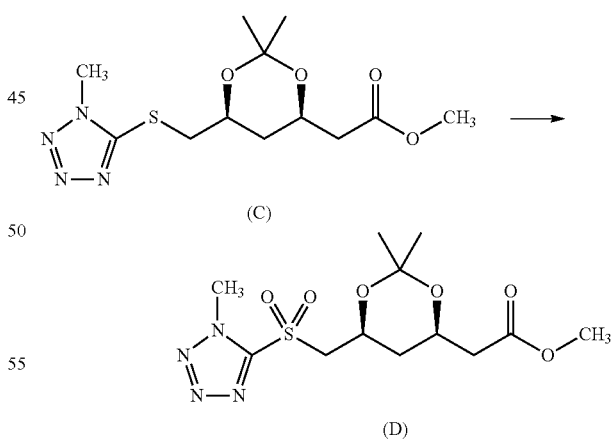

2-((4R,6S)-2,2-Dimethyl-6-((1-methyl-1H-tetrazol-5-ylsulfonyl)methyl)-1,3-dioxan-4-yl)acetic acid methyl ester (C, 31.6 g, 100 mmol). was dissolved in 150 mL of methanol and $Na_2WO_4.2H_2O$ (3.0 g, 10 mol %) was added. The temperature was increased to 40-45° C. Then 32 mL of a 30% $H_2O_2$ solution (310 mmol) was added in 2 h at 40-45° C. When the addition was completed, the mixture was stirred for 2.5 h at 40-45° C. and again 30 mL of 30% $H_2O_2$ was added in 2 h. When the addition was completed, the reaction mixture was cooled to 20-25° C. and left stirring for 18 h. The precipitated solid was isolated by filtration and washed with 50 mL of methanol. After drying 2-((4R,6S)-6-((1-methyl-1H-tetrazole-2-ylsulfonyl)methyl)-2,2-dimethyl-1,3-dioxan-4-yl)acetic acid methyl ester was obtained as a white solid (Compound D, 29.1 g, yield 83%).

$^1$H NMR (300 MHz, CDCl$_3$) δ 4.58-4.50 (m, 1H), 4.38-4.28 (m, 1H) 4.32 (s, 3H), 3.82 (dd, 1H), 3.68 (s, 3H), 3.56 (dd, 1H), 2.45 (ddd, 2H), 1.69 (dt, 1H), 1.42-1.31 (m, 1H), 1.38 (s, 3H), 1.00 (s, 3H).

Example 4

Preparation of 2-((4R,6S)-6-(E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate, methyl ester (F) from N-(4-(4-fluorophenyl)-5-formyl-6-isopropylpyrimidin-2-yl)-N-methylmethanesulfonamide (E) and 2-((4R,6S)-6-((1-methyl-1H-tetrazol-5-ylsulfonyl)methyl)-2,2-dimethyl-1,3-dioxan-4-yl)acetate methyl ester (D)

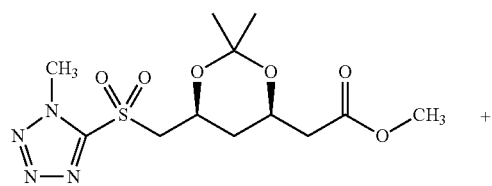

(D)

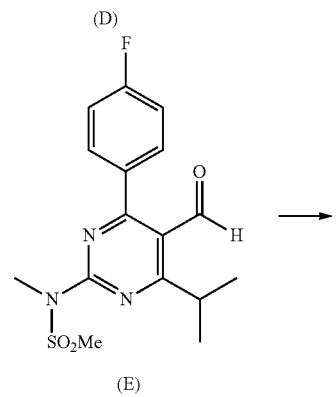

(E)

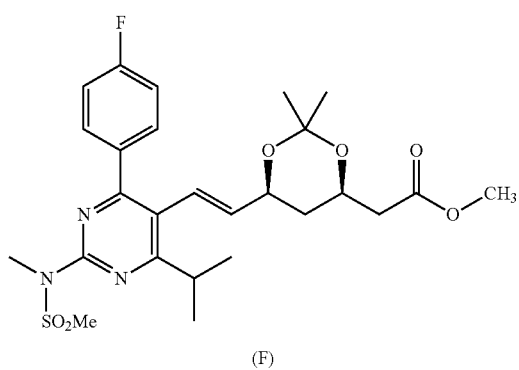

(F)

N-(4-(4-fluorophenyl)-5-formyl-6-isopropylpyrimidin-2-yl)-N-methylmethanesulfonamide (1.0 g, 2.9 mmol) and 2-((4R,6S)-6-(1-methyl-1H-tetrazol-5-ylsulfonyl)methyl)-2,2-dimethyl-1,3-dioxan-4-yl)acetate methyl ester (0.79 g, 2.3 mmol) were added to 10 mL of tetrahydrofuran. The mixture was heated until all reactants were dissolved and then cooled to −60° C. At this temperature 3.3 mL of a NaHMDS solution (1 M in tetrahydrofuran, total 3.3 mmol) was added in 1 h keeping the temperature between −50 and −60° C. When dosing was completed, the temperature was allowed to increase to −10° C. and quenched with 10% aqueous NH$_4$Cl (10 mL). The phases were separated and the organic phase washed successively with 10% aqueous NH$_4$Cl (1×10 ml) and 10% aqueous Na$_2$CO$_3$ (3×10 mL). The organic layer was evaporated to give 2-((4R,6S)-6-(E)-2-(4-(4-fluorophenyl)-6-isopropyl-2-(N-methylmethanesulfonamido)-pyrimidin-5-yl)vinyl-2,2-dimethyl-1,3-dioxan-4-yl)acetate, methyl ester as a solid (Compound F, 0.58 g, 1.1 mmol, 48% yield).

$^1$H NMR (300 MHz, CDCl$_3$) δ 7.66 (dd, 2H), 7.09 (t, 2H), 6.53 (d, 1H), 5.49 (dd, 1H), 4.42-4.21 (m, 2H), 3.72 (s, 3H), 3.58 (s, 3H), 3.52 (s, 3H), 3.49-3.32 (m, 1H), 2.54 (ddd, 2H), 1.59-1.43 (m, 2H), 1.50 (s, 3H), 1.41 (s, 3H), 1.28, (dd, 6H).

Example 5

Preparation of (4R,6S)-6-(chloromethyl)-4-(tetrahydro-2H-pyran-2-yloxy)-tetrahydro-2H-pyran-2-one (H) from (4R,6S)-6-(chloromethyl)-4-hydroxytetrahydro-2H-pyran-2-one (G)

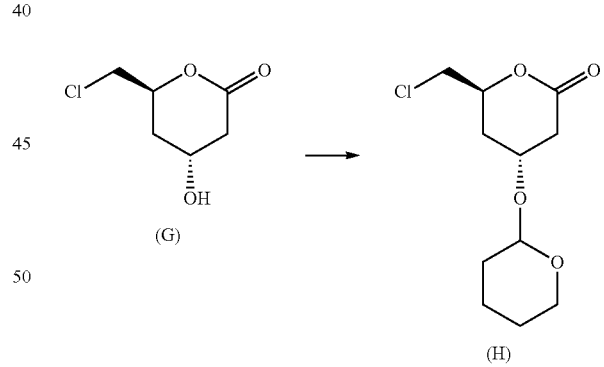

(4R,6S)-6-(chloromethyl)-4-hydroxytetrahydro-2H-pyran-2-one (Compound G, 41.2 g, 0.25 mol) was dissolved in 250 mL of ethyl acetate at 20-25° C. Then 3,4-dihydro-2H-pyran (DHP, 29.4 g, 0.35 mol) was added. The reaction mixture was stirred for 4 h at 20-25° C. The solution was filtered and concentrated to give (4R,6S)-6-(chloromethyl)-4-(tetrahydro-2H-pyran-2-yloxy)-tetrahydro-2H-pyran-2-one (Compound H, 64.2 g, quantitative yield) as a greyish oil, which was used as such in the next step.

Example 6a

Preparation of (4R,6S)-6-((benzo[6]thiazole-2-ylthio)methyl)-4-(tetrahydro-2H-pyran-2-yloxy)-tetrahydro-2H-pyran-2-one (I) from (4R,6S)-6-(chloromethyl)-4-(tetrahydro-2H-pyran-2-yloxy)-tetrahydro-2H-pyran-2-one (H) and 2-mercapto-1H-benzothiazole (2-MBT)

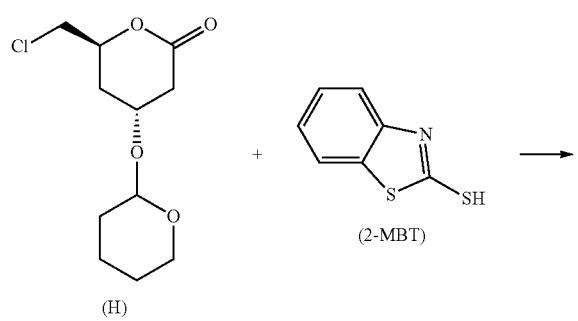

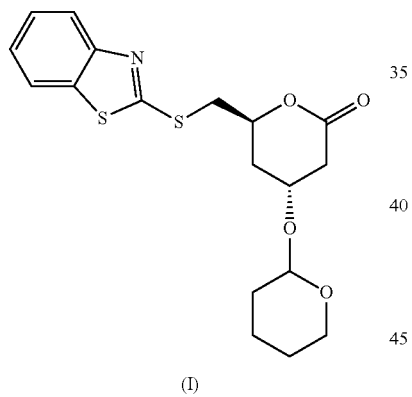

(4R,6S)-6-(chloromethyl)-4-(tetrahydro-2H-pyran-2-yloxy)-tetrahydro-2H-pyran-2-one (H, 24.7 g, 100 mmol) was dissolved in 150 mL of NMP. Then NaHCO$_3$ (12.6 g, 150 mmol) and 2-MBT (21.7 g, 130 mmol) were added, followed by 50 mL of NMP. The mixture was heated for 2 h at 70° C. and then for 7 h at 90° C. After cooling to 20-25° C., MTBE was added (300 mL) and saturated aqueous NaHCO$_3$ (300 mL). The organic layer was separated and the aqueous layer washed with MTBE (2×100 mL). The combined organic phases were washed successively with 200 mL of saturated aqueous NaHCO$_3$ and 200 mL water. After drying over Na$_2$SO$_4$, the organic phase was concentrated to give (4R,6S)-6-((benzo[6]thiazole-2-ylthio)methyl)-4-(tetrahydro-2H-pyran-2-yloxy)-tetrahydro-2H-pyran-2-one (I, 24.4 g, 64.2 mmol, yield 64.2%), as brownish oil, which was used as such in the next step.

Tentative Example 6b

Preparation of (4R,6S)-6-((1-methyl-1H-tetrazol-5-ylthio)methyl)-4-(tetrahydro-2H-pyran-2-yloxy)-tetrahydro-2H-pyran-2-one (J) from (4R,6S)-6-(chloromethyl)-4-(tetrahydro-2H-pyran-2-yloxy)-tetrahydro-2H-pyran-2-one (H) and 1-methyl-1H-tetrazole-5-thiol (MTT)

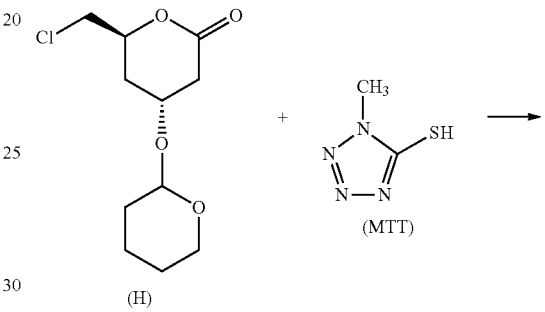

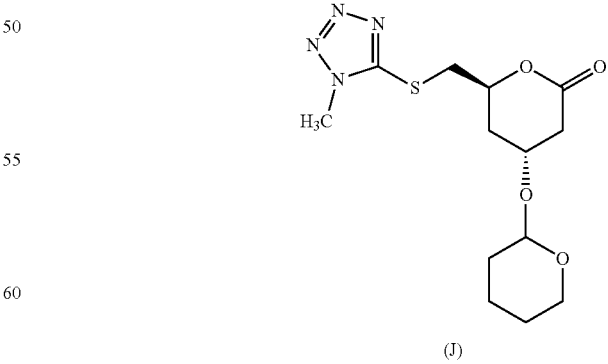

Example 6a was repeated with MTT instead of 2-MBT to give (4R,6S)-6-(1-methyl-1H-tetrazol-5-ylthio)methyl)-4-

(tetrahydro-2H-pyran-2-yloxy)-tetrahydro-2H-pyran-2-one (J) which was used in Example 7b.

Example 7a

Preparation of (4R,6S)-6-((benzo[6]thiazole-2-ylsulfonyl)methyl)-4-(tetrahydro-2H-pyran-2-yloxy)-tetrahydro-2H-pyran-2-one (K) from (4R,6S)-6-((benzo[6]thiazole-2-ylthio)methyl)-4-(tetrahydro-2H-pyran-2-yloxy)-tetrahydro-2H-pyran-2-one (I)

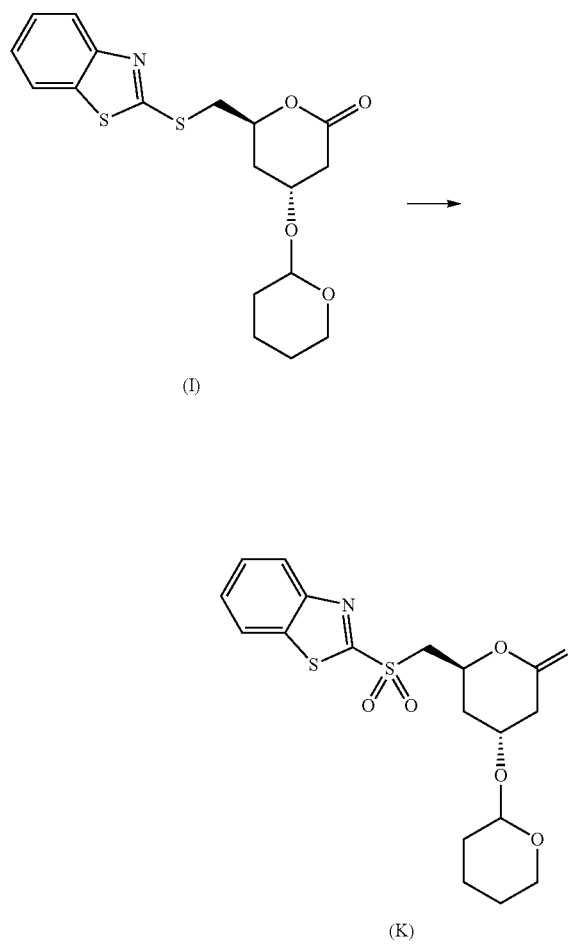

(4R,6S)-6-((benzo[6]thiazole-2-ylthio)methyl)-4-(tetrahydro-2H-pyran-2-yloxy)-tetrahydro-2H-pyran-2-one (Compound I 23.0 g, estimated purity 70%, 42 mmol) was dissolved in 200 mL of $CH_2Cl_2$. The solution was cooled to 0° C., followed by addition of $NaHCO_3$ (14.1 g, 168 mmol). Then in 2 h, MCPBA (meta-chloroperbenzoic acid, 27.6 g, 112 mmol, 70% purity) was added, keeping the temperature between 0 and 5° C. The thick slurry was stirred for 18 h allowing the temperature to increase to 20-25° C., followed by addition of 150 mL of $CH_2Cl_2$ and 150 mL of saturated aqueous $NaHCO_3$. The organic phase was separated and washed with 3×50 mL of saturated aqueous $NaHCO_3$. After drying over $Na_2SO_4$, the organic phase was concentrated to give the crude compound of formula (K) as thick yellow oil (25.0 g, 60% pure, 36 mmol, yield 87%).

Tentative Example 7b

Preparation of (4R,6S)-6-((1-methyl-1H-tetrazol-5-ylsulfonyl)methyl)-4-(tetrahydro-2H-pyran-2-yloxy)-tetrahydro-2H-pyran-2-one (L) from (4R,6S)-6-((1-methyl-1H-tetrazol-5-ylthio)methyl)-4-(tetrahydro-2H-pyran-2-yloxy)-tetrahydro-2H-pyran-2-one (J)

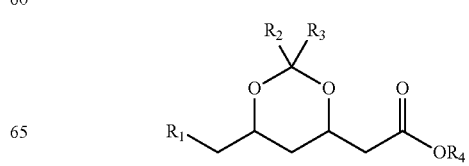

Example 7a was repeated with Compound (J) instead of (I) to give (4R,6S)-6-((1-methyl-1H-tetrazol-5-ylsulfonyl)methyl)-4-(tetrahydro-2H-pyran-2-yloxy)-tetrahydro-2H-pyran-2-one (L).

The invention claimed is:

1. A process for preparing a sulfone comprising the steps of:

(a) reacting a halomethyl substrate of general formula (1a) or (1b),

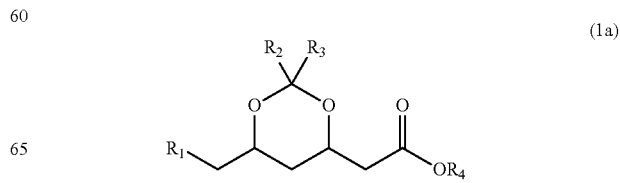

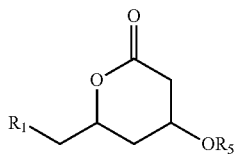

wherein $R_1$ is halogen, wherein $R_2$ and $R_3$ each independently stand for an alkyl with 1 to 12 carbon atoms or an alkenyl with 1 to 12 carbon atoms or a cycloalkyl with 3 to 7 carbon atoms or a cycloalkenyl with 3 to 7 carbon atoms or an aryl with 6 to 10 carbon atoms or an aralkyl with 7 to 12 carbon atoms or wherein $R_2$ and $R_3$ form a ring together with the carbon atom to which they are bound, wherein $R_4$ is an alkyl or alkenyl group with 1 to 4 four carbon atoms and wherein $R_5$ is an alcohol protecting group, with 1-methyl-1H-tetrazole-5-thiol or a salt thereof to obtain a compound of general formula (2a) or (2b), respectively;

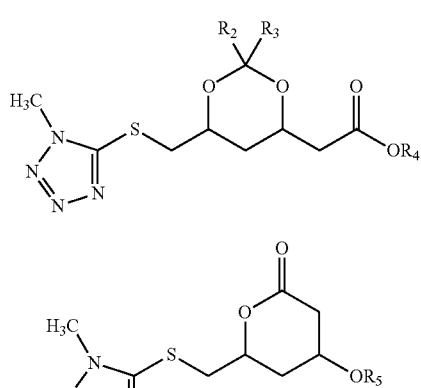

and thereafter, (b) oxidizing the compound of general formula (2a) or (2b) to give a sulfone of general formula (3a) or (3b), respectively,

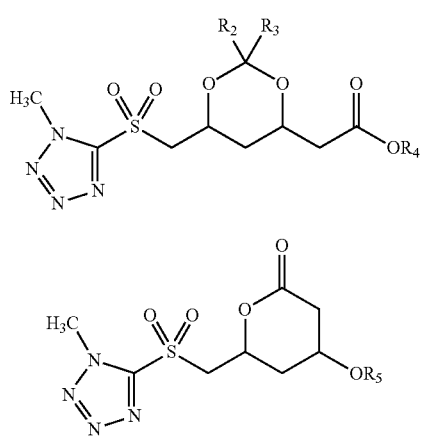

wherein $R_2$, $R_3$ and $R_4$ in formulas (2a), (2b), (3a) and (3b) are the same as previously defined for formulas (1a) and (1b).

2. The process according to claim 1 wherein $R_1$ is bromine or chlorine, $R_2$ is ethyl or methyl and $R_3$ is ethyl or methyl or $R_2$ and $R_3$ form a cyclopentyl ring or a cyclohexyl ring together with the carbon atom to which they are bound, $R_4$ is sec-butyl, tert-butyl, ethyl, methyl, or iso-propyl and $R_5$ is methoxyethoxymethyl, tetrahydrofuranyl or tetrahydropyranyl.

3. The process according to claim 1, which further comprises isolating the compound of the general formula (2a) or (2b) and/or the compound of general formula (3a) or (3b).

4. The process according to claim 1, wherein step (b) is carried out in the presence of hydrogen peroxide or a peracid or bleach or tert-BuOCl or a perborate or an N-oxide or a permanganate or a chromate or a chlorate or a bromate or a perchlorate or a periodate or tert-butyl hydroperoxide or oxone or a peroxodisulfate or oxygen or mixtures thereof.

5. The process according to claim 1, which further comprises:

(c) reacting the sulfone of general formula (3a) or (3b) with a compound of general formula $R_6$—CH=O, wherein $R_6$ is 4-(4-fluorophenyl)-2,6-diisopropyl-5-(methoxymethyl)nicotinaldehyde or 3-(4-fluorophenyl)-1-isopropyl-1H-indole-2-carbaldehyde or 2-cyclopropyl-4-(4-fluorophenyl)quinoline-3-carbaldehyde or N-(4-(4-fluorophenyl)-5-formyl-6-isopropylpyrimidin-2-yl)-N-methylmethanesulfonamide to give a compound of general formula (4a) or (4b), respectively,

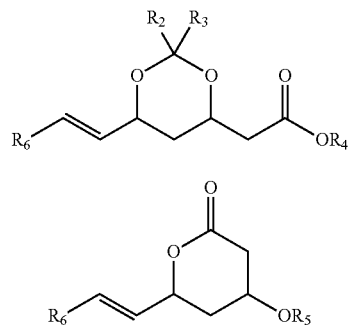

wherein $R_2$, $R_3$ and $R_4$ in formulas (4a) and (4b) are the same as previously defined for formulas (1a) and (1b).

6. The process according to claim 5, which is carried out in the presence of a sodium-comprising base.

7. The process according to claim 6, wherein the sodium-comprising base is sodium hexamethyldisilazane.

8. The process according to claim 5, which further comprises deprotecting and isolating the formulas (4a) and (4b).

9. A compound of general formula (6),

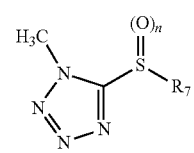

wherein
n is 0, 1 or 2, and wherein
$R_7$ is a radical of formula (7) or (8),

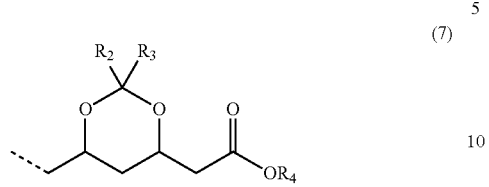
(7)

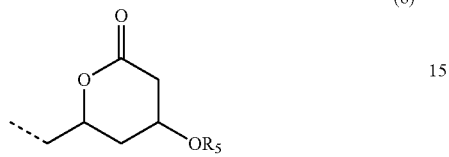
(8)

wherein $R_2$ and $R_3$ each independently stand for an alkyl with 1 to 12 carbon atoms or an alkenyl with 1 to 12 carbon atoms or a cycloalkyl with 3 to 7 carbon atoms or a cycloalkenyl with 3 to 7 carbon atoms or an aryl with 6 to 10 carbon atoms or an aralkyl with 7 to 12 carbon atoms or wherein $R_2$ and $R_3$ form a ring together with the carbon atom to which they are bound, wherein $R_4$ is an alkyl or alkenyl group with 1 to 4 four carbon atoms and wherein $R_5$ is an alcohol protecting group.

* * * * *